(12) United States Patent
Gunawan et al.

(10) Patent No.: US 9,772,385 B2
(45) Date of Patent: *Sep. 26, 2017

(54) ROTATING MAGNETIC FIELD HALL MEASUREMENT SYSTEM

(71) Applicant: International Business Machines Corporation, Armonk, NY (US)

(72) Inventors: Oki Gunawan, Westwood, NJ (US); Michael A. Pereira, Mohegan Lake, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 29 days.

This patent is subject to a terminal disclaimer.

(21) Appl. No.: 14/748,495

(22) Filed: Jun. 24, 2015

(65) Prior Publication Data

US 2016/0299201 A1    Oct. 13, 2016

Related U.S. Application Data

(63) Continuation of application No. 14/682,696, filed on Apr. 9, 2015.

(51) Int. Cl.
G01R 33/07 (2006.01)
G01N 27/72 (2006.01)

(52) U.S. Cl.
CPC ........... G01R 33/072 (2013.01); G01N 27/72 (2013.01); G01R 33/07 (2013.01)

(58) Field of Classification Search
CPC ......... G01D 5/145; G01N 27/72; B01R 33/07
(Continued)

(56) References Cited

U.S. PATENT DOCUMENTS 6,576,890 B2 * 6/2003 Lin .................. G01D 5/145
250/231.14
9,041,389 B2   5/2015 Gokmen et al.
(Continued)

FOREIGN PATENT DOCUMENTS

JP    2003207365    * 7/2003

OTHER PUBLICATIONS

List of IBM Patents or Patent Applications Treated as Related; (Appendix P), Filed Aug. 5, 2015; 2 pages.
(Continued)

*Primary Examiner* — Reena Aurora
(74) *Attorney, Agent, or Firm* — Cantor Colburn LLP; Vazken Alexanian (57) ABSTRACT

A rotating magnetic field Hall apparatus is provided and includes first and second magnets disposed in a master-slave configuration, a device-under-test (DUT) stage interposable between the first and second magnets on which a DUT is disposable in first or second orientations for Hall measurement or photoelectromagnetic (PEM) testing, respectively, controllers disposed to center the DUT stage between the first and second magnets and orthogonal magnetic field sensors disposed aside lateral sides of the first magnet to facilitate positional initialization of the first and second magnets and to generate in-phase and out-of-phase reference signals for phase-sensitive or lock-in Hall signal detection. The system also includes software system to perform signal processing to yield the final Hall signal.

7 Claims, 6 Drawing Sheets

(58) Field of Classification Search
USPC .................................................... 324/207.2
See application file for complete search history.

(56) References Cited

U.S. PATENT DOCUMENTS

2008/0088304 A1* 4/2008 Coulter .............. G01R 33/1215
  324/263
2014/0028305 A1 1/2014 Gokmen et al.

OTHER PUBLICATIONS

Oki Gunawan et al., "Rotating Magnetic Field Hall Measurement System", U.S. Appl. No. 14/682,696, filed Apr. 9, 2015.

* cited by examiner

ROTATING MAGNETIC FIELD HALL MEASUREMENT SYSTEM

This application is a continuation of U.S. application Ser. No. 14/682,696, which was filed on Apr. 9, 2015. The entire disclosures of U.S. application Ser. No. 14/682,696 are incorporated herein by reference.

BACKGROUND

The present disclosure relates generally to measurement techniques, and more specifically, to a Hall measurement system with a rotary magnet.

Hall measurement is a characterization technique that may be used in a variety of applications, such as semiconductor and solid state device research. Hall measurement enables measurement of a free carrier density, which may yield carrier mobility when considered together with a resistivity measurement. The so-called Hall effect occurs when a current is passed through a material with an applied perpendicular magnetic field, such that a Hall voltage $V_H$ is generated, as provided in equation #1 as follows:

$$V_H = BI/nde \qquad \text{Eq. #1}$$

In equation #1 above, B is the magnetic field, I is the electric current passing through the sample, n is the free carrier density, d is the sample thickness and e is the charge of an electron.

A figure of merit in the Hall measurement is the Hall angle $\phi$, whose tangent is defined as the ratio between the Hall or transverse resistance ($R_{xy}$) and the longitudinal resistance ($R_{xx}$). The tangent of this Hall angle, in the case of a square sample, may be given by equation #2 as follows:

$$\tan \phi = R_{xy}/R_{xx} = B\mu \qquad \text{Eq. #2}$$

In equation #2 above, $\mu$ is the mobility of the majority carrier.

A good or quality Hall measurement requires a sufficiently large Hall angle or tan $\phi$ on the order of unity. Based on equation #2, a problem may arise when a sample has poor mobility (e.g., $\mu \ll 1$ cm$^2$/Vs) or the magnetic field that is available is limited (e.g., B$\ll$0.1 Tesla). Furthermore, based on equation #1, samples with a very high carrier density n may also cause a small Hall voltage $V_H$. Some measurement environments, such as low temperature measurement, dictate the use of a very small excitation current I, thus resulting in a small Hall voltage $V_H$. In such situations, a DC magnetic field Hall measurement may yield a small Hall voltage $V_H$ buried within a large DC voltage offset due to sample geometrical asymmetry. The asymmetry may cause a mixing of the Hall or transverse resistance ($R_{xy}$) and the longitudinal resistance ($R_{xx}$).

SUMMARY

According to one embodiment of the present invention, a rotating magnetic field Hall apparatus is provided and includes first and second magnets disposed in a master-slave configuration, a device-under-test (DUT) stage interposable between the first and second magnets on which a DUT is disposable in first or second orientations for Hall measurement or photoelectromagnetic (PEM) testing, respectively, controllers disposed to center the DUT stage between the first and second magnets and orthogonal magnetic field sensors disposed aside lateral sides of the first magnet to facilitate positional initialization of the first and second magnets and to generate in-phase and out-of-phase reference signals for phase-sensitive or lock-in Hall signal detection.

According to another embodiment of the present invention, a rotating magnetic field Hall apparatus is provided and includes a motor-driven cylindrical magnet with transverse magnetization, a freely rotating cylindrical magnet, which rotates with the motor-driven magnet, a device-under-test (DUT) stage interposable between the motor-driven and freely rotating magnets on which a DUT is disposable in first or second orientations for Hall measurement or photoelectromagnetic (PEM) testing, respectively, first and second controllers disposed to respectively maneuver the motor-driven magnet and the DUT stage and orthogonal magnetic field sensors disposed to facilitate positional initialization of the motor-driven and freely rotating magnets and to generate in-phase and out-of-phase reference signals for phase-sensitive or lock-in Hall signal detection.

According to yet another embodiment of the present invention, a computing system is provided and includes a processor and a memory on which a program is stored, which, when executed causes the processor to manage a rotating magnetic field Hall apparatus. The apparatus includes first and second magnets disposed in a master-slave configuration, a device-under-test (DUT) stage interposable between the first and second magnets on which a DUT is disposable in first or second orientations for Hall measurement or photoelectromagnetic (PEM) testing, respectively, controllers operable by the processor and disposable to center the DUT stage between the first and second magnets, and orthogonal magnetic field sensors operable by the processor and disposable aside lateral sides of the first magnet to facilitate positional initialization of the first and second magnets and to generate in-phase and out-of-phase reference signals for phase-sensitive or lock-in Hall signal detection.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

As will be described below, a rotating magnetic field Hall and photoelectromagnet (PEM) system with high sensitivity are provided. The system is targeted for materials with very low carrier mobility, very thin samples, very low or very high carrier density samples and includes a pair of rotating magnets, one driven by a motor drive and another one that rotates freely and can be positioned by a linear actuator tower, magnetic focusing pieces, a manipulator to position the sample, light source to illuminate the sample, mechanical platform with connector panels and an enclosure shield. The system is connected to a motor control box and a switch matrix system and is controlled by a computer. Software performing signal processing (power spectral density and lock-in detection) is used to extract the final Hall or PEM signal. The system can also be used to improve signal to noise ratio of any experiments involving magnetic field.

The following disclosure is related to the disclosures of U.S. Pat. No. 8,895,355 (Cao), U.S. Patent Application No. 2014/0028305 (Gokmen) and Gunawan, et al., "Parallel Dipole Line System," Applied Physics Letters 106, 062 407 (2015). The entire disclosures of these documents are incorporated herein by reference.

Figure 1:
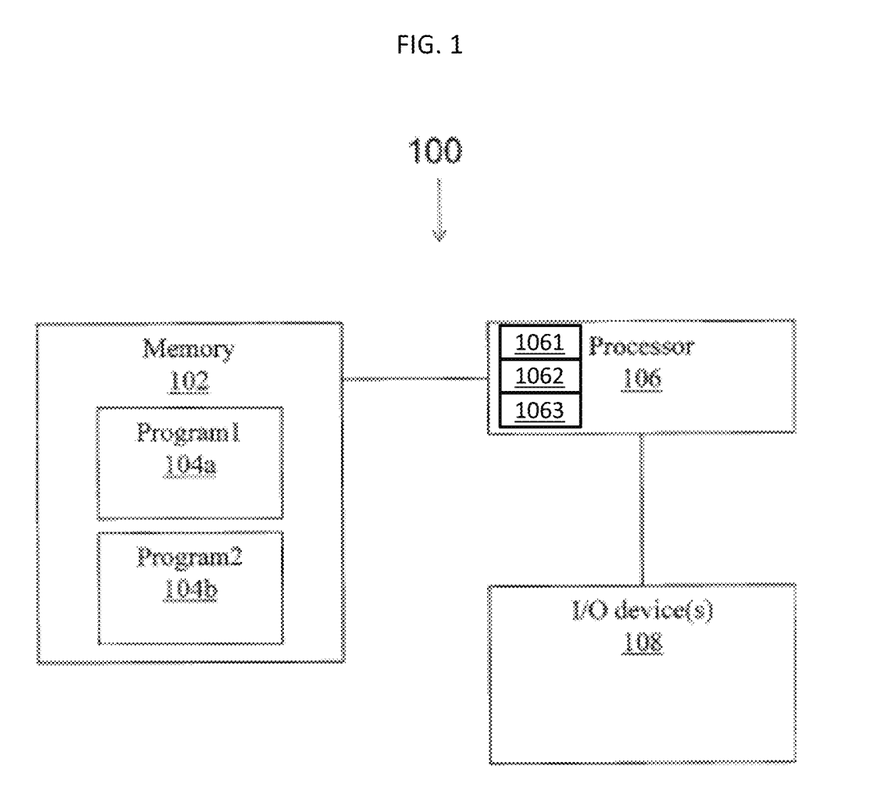
FIG. 1 is a schematic diagram illustrating a computing system in accordance with embodiments.

Referring to FIG. 1, an exemplary computing system 100 is shown. The system 100 is shown as including a memory 102. The memory 102 may store executable instructions that may be stored or organized in any manner and at any level of abstraction, such as in connection with one or more processes, routines, methods, etc. As an example, at least a portion of the instructions are shown in FIG. 1 as being associated with a first program 104a and a second program 104b.

The instructions stored in the memory 102 may be executed by one or more processors, such as a processor 106. The processor 106 may be coupled to one or more input/output (I/O) devices 108 and includes a signal conditioning system 1061 for data selection and background subtraction, a power spectral density analysis system 1062 and a system for lock-in detection and signal-to-noise ratio calculation 1063. In some embodiments, the I/O device(s) 108 may include one or more of a keyboard, a touchscreen, a display screen, a microphone, a speaker, a mouse, a button, a remote control, a joystick, a printer, etc. The I/O device(s) 108 may be configured to provide an interface to allow a user to interact with the system 100. The system 100 is illustrative. In some embodiments, one or more of the entities may be optional. In some embodiments, additional entities not shown may be included. For example, in some embodiments the system 100 may be associated with one or more networks, which may be communicatively coupled to one another via one or more switches, routers or the like. In some embodiments, the entities may be arranged or organized in a manner different from what is shown in FIG. 1. One or more of the entities shown in FIG. 1 may be associated with one or more of the devices or entities described herein.

Figure 2:
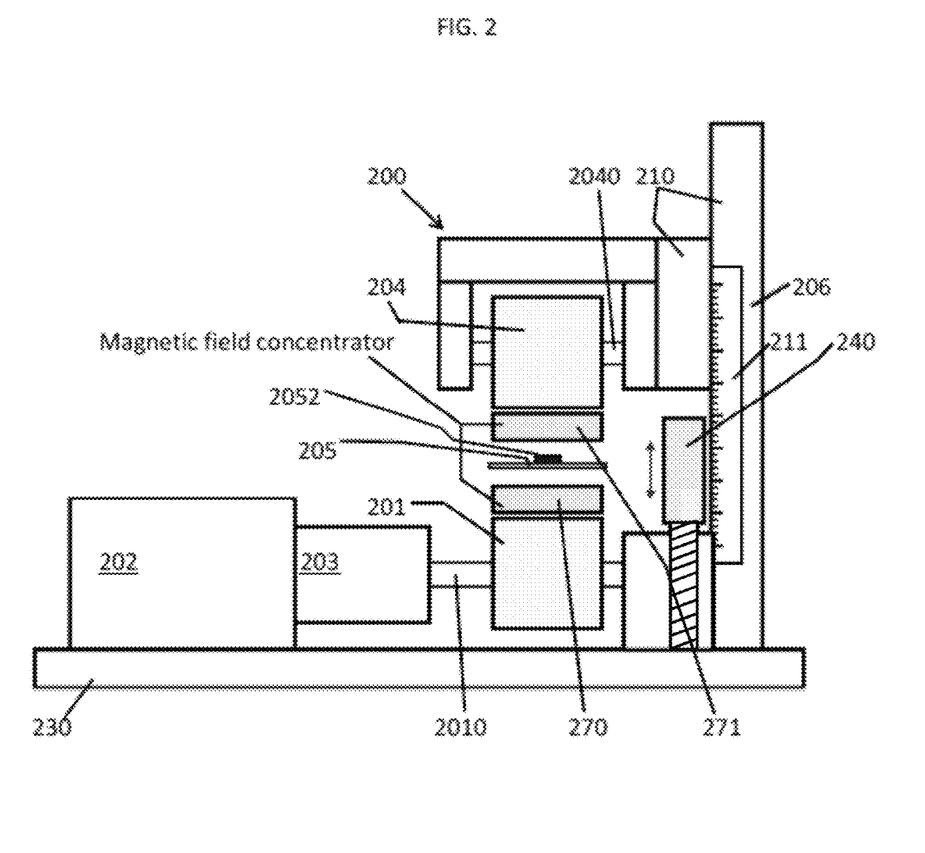
FIG. 2 is a side view of a rotating magnetic field Hall apparatus in accordance with embodiments.
Figure 3:
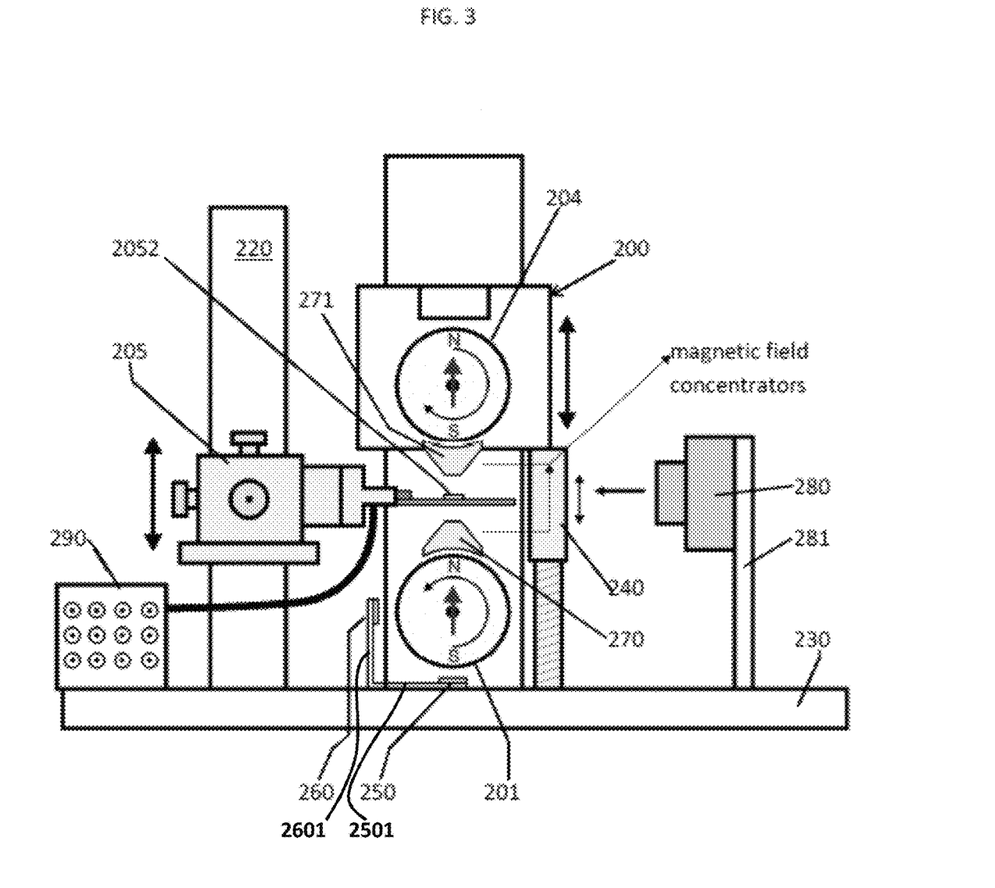
FIG. 3 is a front view of a rotating magnetic field Hall apparatus in accordance with embodiments.
Figure 4A:
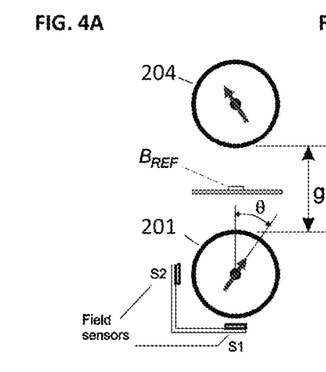
FIG. 4A is a graphical illustration of magnet initialization and field determination.
Figure 4B:
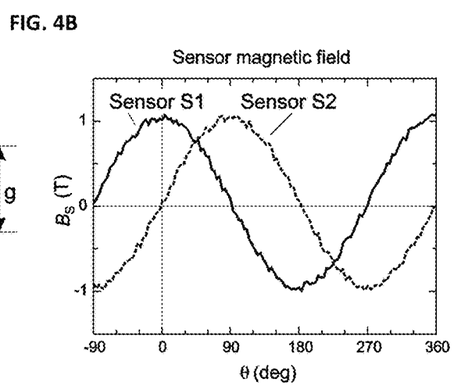
FIG. 4B is a graphical illustration of magnet initialization and field determination.

FIGS. 2 and 3 illustrate a system architecture 200 that may be used as a rotary magnetic field Hall measurement system. The architecture 200 may be operative in connection with one or more devices or entities, such as the devices and entities described above in connection with the system 100 of FIG. 1. As shown in FIGS. 2 and 3, the architecture 200 may be provided as a rotating magnetic field Hall apparatus and includes a first or motor-driven cylindrical magnet 201, which is driven to rotate by a motor 202 via a gearbox 203, a second or freely rotating cylindrical magnet 204, which rotates with the motor-driven magnet 201 in a master-slave configuration in which the driving of the motor-driven magnet 201 and its resultant rotation drives a corresponding rotation of the freely rotating magnet 204, a device-under-test (DUT) stage 205, first and second controllers 206 and 207 and orthogonal magnetic field sensor system 208. The motor-driven magnet 201 and the freely rotating magnet 204 may each be cylindrical magnets with transverse (diametric) magnetization (i.e. magnetization along the diameter). They form a rotating master-slave magnet system that produces several important characteristics including a unidirectional field at the center of the DUT 2052 (to be described below), high purity single harmonic field oscillation and strong magnetic fields (i.e., about ~2 T peak-to-peak).

The DUT stage 205 is interposable between the motor-driven magnet 201 and the freely rotating magnet 204 and has a surface on which a DUT 2052 is disposable. The DUT 2052 may be provided as a Hall or van der Pauw sample with 4 or more terminals for receipt of current and may be mounted in first or second orientations. For example, when the DUT 2052 is mounted horizontally, the DUT 2052 may be positioned for Hall measurement. Conversely, as another example, when the DUT 2052 is mounted vertically, the DUT 2052 may be positioned for photoelectromagnetic (PEM) testing with light coming from a side as will be described below.

The first controller 206 is provided as a magnet tower 210 and is disposed to maneuver at least one of the motor-drive magnet 201 and the freely rotating magnet 204 in at least a first dimension, such as a vertical or Z-axis dimension. The second controller 207 is provided as a stage tower 220 and is disposed to maneuver the DUT stage 205 in the first dimension as well as second and third dimensions, such as lateral or X- and Y-axis dimensions. In accordance with embodiments, both the magnet tower 210 and the stage tower 220 may be affixed to a platform 230, which is substantially planar, so that they stand side-by-side with a relatively small distance between them. The motor 202 may also be affixed to the platform 230 for support. The magnet tower 210 and the stage tower 220 are both elongate features that extend in the first dimension (i.e., upwardly) from the platform 230.

The magnet tower 210 includes a ruler feature 211 that facilitates a measurement of a distance between the motor-driven magnet 201 and the freely rotating magnet 204 and between either magnet and the DUT stage 205 or the DUT 2052. A stopper 240 is also affixed to the platform 230 to limit a distance the freely rotating magnet 204 can travel. The stopper 240 includes a threaded shaft and a correspondingly threaded stopper element, which can be rotated about the shaft to assume a predefined position. At this position, an upper surface of the stopper element serves as a mechanical interference device that prevents movement of the freely rotating magnet 204 toward the DUT 2052 beyond a given distance.

In accordance with embodiments, the motor-driven magnet 201 is a cylindrical magnet that is rotatably disposed on a driveshaft 2010 that extends from the gearbox 203 to a support feature affixed to the platform 230 to define a first rotational axis. The motor-driven magnet 201 thus rotates about the first rotational axis in accordance rotational drive inputs provided by the motor 202 via the gearbox 203. The freely-rotating magnet 204 is a cylindrical magnet that is rotatably disposed on a shaft 2040 that extends through the freely rotating magnet 204 between support flanges affixed to the magnet tower 210 to define a second rotational axis about which the freely rotating magnet 204 rotates. The motor-driven magnet 201 and the freely rotating magnet 204 may be substantially parallel with one another with the first and second rotational axes being correspondingly substantially parallel with one another. The freely rotating magnet 204 rotates as a result of its interaction with the magnetic field generated by the rotation of the motor-driven magnet 201.

The orthogonal magnetic field sensor system 208 includes a first sensor 250 and a second sensor 260. The first sensor 250 sits at a distal end of a first spire 2501 and may be disposed to face a lower facing lateral (i.e., non-longitudinal) surface of the motor-driven magnet 201. Thus, the first sensor 250 may face upwardly in the first dimension. The second sensor 260 sits at a distal end of a second spire 2601, which is oriented transversely relative to the first spire 2501, and may be disposed to face a sideways facing lateral side of the motor-driven magnet 201. Thus, the second sensor 260 may face sideways in either of the second or third dimensions. In any case, the first sensor 201 and the second sensor 204 cooperatively facilitate positional initialization of the motor-driven magnet 201 and possibly the freely rotating magnet 204. The first sensor 201 and the second sensor 204 may be further configured to generate in-phase and out-of-phase reference signals for phase-sensitive or lock-in Hall signal detection operations.

As the motor-driven magnet 201 rotates about the first rotational axis, the motor-driven magnet 201 generates a magnetic field in the vicinity of the DUT stage 205. Similarly, as the freely rotating magnet 204 rotates about the second rotational axis, the freely rotating magnet 204 generates a magnetic field in the vicinity of the DUT stage 205. At least one or both of these two magnetic fields can, in some case, be increased by the presence of a magnetic flux concentrator. The magnetic flux concentrator may be provided as a first magnetic flux concentrator 270 and a second magnetic field concentrator 271. The first magnetic field concentrator 270 is interposed between the motor-driven magnet 201 and a lower surface of the DUT stage 205. Conversely, the second magnetic flux concentrator 271 is interposed between the freely-rotating magnet 204 and the DUT stage 205 or an upper surface of the DUT 2052 itself.

In accordance with embodiments, the first and the second magnetic flux concentrators 270 and 271 may be formed of a high permeability material, such as a material including iron-nickel or alloys thereof.

Still referring to FIGS. 2 and 3, the architecture 200 may further include a light source 280 and a contact terminal 290. The light source 280 is supported on a distal end of a support member 281 that is affixed to the platform 230 and is disposed to emit light toward the DUT 2052 for execution of a PEM operation. The contact terminal 290 may be affixed directly to the platform 230 and serves to provide and direct current to the DUT 2052 during testing operations.

With reference to FIGS. 4A-7, the system represented by the architecture 200 of FIGS. 1 and 2 may be operated in first or second modes. The first mode is a static (i.e., direct current or DC) magnetic field mode or a standard static field Hall system in which the field on the DUT 2052 is held stationary (e.g., +−$B_{max}$, 0) and Hall measurement is performed. The second mode is a continuous rotation (i.e., alternating current or AC) field mode, where the field continuously rotates and Hall measurement is performed. As noted above, during the second mode, the orthogonal magnetic field sensor system 208 initializes magnet positions to determine a zero angle ($\theta=0$) where the magnetic field on the DUT 2052 is at a maximum. This position can be more accurately determined by monitoring when the second sensor 260 has a zero angle because at this position the first sensor 250 is near maximum.

An operation of the architecture will now be described with the understanding that amplitude of field oscillation ($B_{max}$) on the DUT 2052 is important to be determined accurately as it will affect the accuracy of Hall measurement. As the motor-driven and freely rotating magnets 201 and 204 rotate and the corresponding magnetic fields rotate, a phase angle of at least the motor-driven magnet 201 is given as: $\theta=\omega_{REF}t$, where $\omega=2\pi f_{REF}$ and $f_{REF}$ is a reference rotation frequency and t is time. The reference magnetic field on the DUT 2052 is given as:

$$B_{REF}(t)=B_{max}\cos(\omega_{REF}t)$$

$B_{max}$ is an average field over the DUT 2052 and depends on the gap g between the motor-driven and freely rotating magnets 201 and 204 and a size s of the DUT 2052. The gap g can be determined from the ruler feature 211 reading on the magnet tower 210. $B_{max}$ can be determined using the equation of a magnetic field of a diametric magnet. Assuming that a size s×s DUT 2052 placed at the plane y-z at the center of the gap g, the field is given as:

$$v^2 = (g/2 - a\cos\phi)^2 + (y - a\sin\phi)^2$$

$$B_M(y, z) = \frac{\mu_0 Ma}{2\pi} \int_0^{2\pi} \sum_{n=1,2} \frac{(-1)^n(g/2 - a\cos\phi)\cos\phi}{u_n^2 + v^2 + u_n\sqrt{u_n^2 + v^2}} d\phi \hat{x}$$

$$u_{1,2} = z \pm L/2$$

The average maximum field is averaged over the sample size:

$$B_{max}(g, s) = \int B_M(y, z) dy dz / s^2$$

Figure 5A:
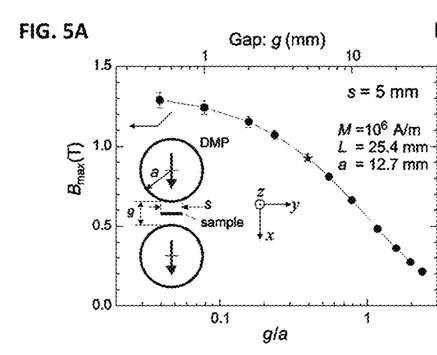
FIG. 5A is a graphical illustration of magnet field determination on a device under test (DUT)
Figure 5B:
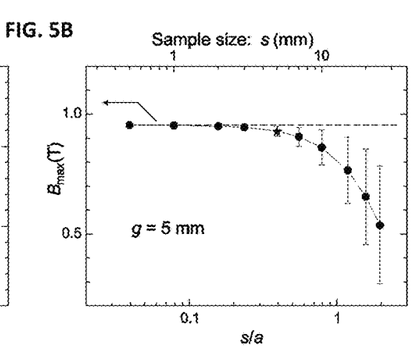
FIG. 5B is a graphical illustration of magnet field determination on a device under test (DUT)

Examples of the magnetic field determination are shown in the plots of FIGS. 5A and 5B. FIG. 5A shows that $B_{max}$ drops as the gap g grows and FIG. 5B also shows that $B_{max}$ drops as the size s of the DUT 2052 gets larger. Thus, $B_{max}$ can be determined using these plots or the equations given above, given magnet magnetization M, length L, radius a, gap g and DUT 2052 size s.

Figure 6:
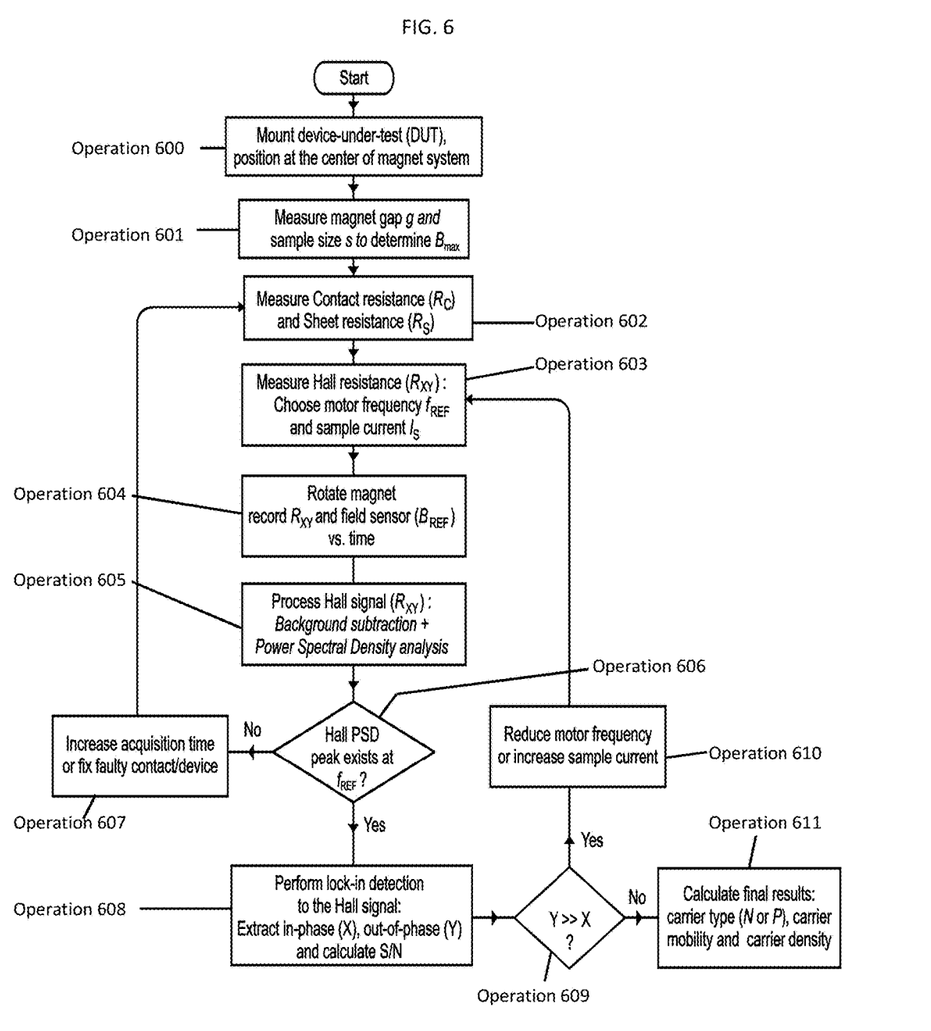
FIG. 6 is a flow diagram illustrating a method of operating the rotating magnetic field Hall apparatus of FIGS. 1 and 2.
Figure 7:
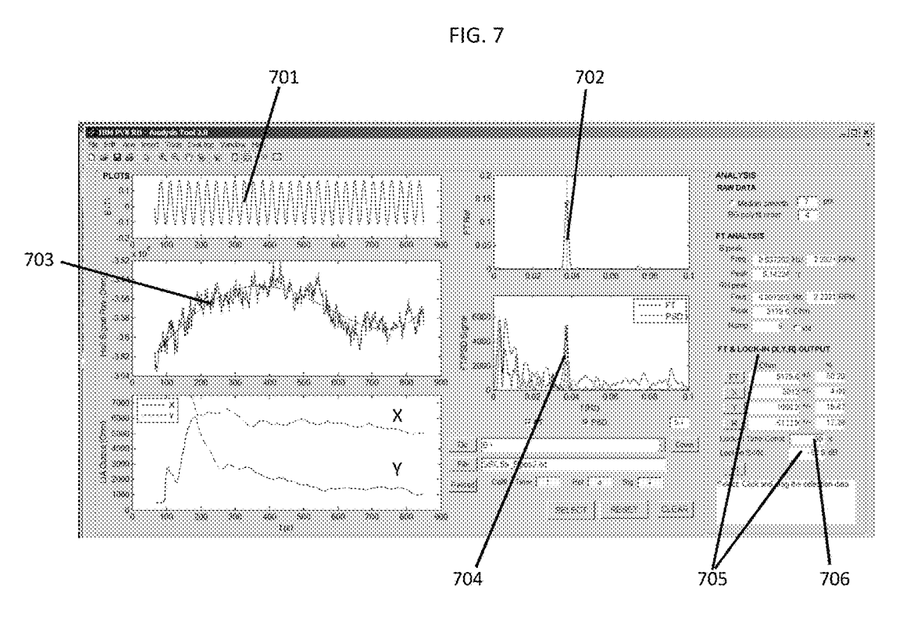
FIG. 7 is an exemplary screenshot generated by control software in accordance with embodiments.

With reference back to FIG. 1 and with additional reference to FIGS. 6 and 7 and with the understanding that the processor 106 and the I/O device(s) may be employed to control and communicate with the various components of the architecture 200 and that at least one or both of first program 104a and a second program 104b may be configured as control software for management of the various components of the architecture 200, the control software may execute a method. The method starts with the DUT 2052 being mounted generally at a center of the DUT stage 205 (operation 600), a measurement of the gap g and the size s of the DUT 2052 to determine $B_{max}$ (operation 601) and a measurement of contact resistance ($R_C$) and sheet resistance ($R_S$) of the DUT 2052 (operation 602). The method continues with a measurement of Hall resistance ($R_{XY}$) and a choosing of a motor frequency $f_{REF}$ and a sample current $I_S$ for the motor-driven magnet 201 (operation 603), a rotation of the motor-driven magnet 201 and a recording of Hall resistance ($R_{XY}$) and field sensor $B_{REF}$ versus time (operation 604) and a processing of the Hall signal ($R_{XY}$) by way of a background subtraction and a power spectral analysis (operation 605).

For the processing of the Hall signal ($R_{XY}$) of operation 605, manual or automatic raw data selection is executed to avoid transient or spiky signals that may be deleterious to final phase-sensitive-detector outputs, background data is removed, Fourier transform (FT) and power-spectral-density (PSD) analyses are conducted to permit numerical phase sensitive detection/lock-in analysis of the raw signal as well as calculation of the signal to noise ratio (S/N).

The raw Hall signal is given as:

$$R_{XY}(t) = \frac{B_{max}\cos\omega t}{nde} + \frac{B_{max}\omega A}{I_S}\sin\omega t + \alpha R_{XX} + N(t)$$

where $R_{XY}$ is the raw transverse resistance or Hall signal, $R_{XX}$ is the longitudinal resistance, n is a carrier density, d is DUT 2052 thickness, e is an electron charge, A is an effective loop area, is $I_S$ is a current source passing through the DUT 2052, $\alpha$ is a fraction of $R_{XX}$ that appears in $R_{XY}$ ($0<\alpha<1$) due to DUT 2052 asymmetry and N(t) is noise or the rest of the signal.

The control software will then perform numerical phase-in detection to separate the in-phase signal X (the desired Hall signal) and the out-of-phase signal Y (parasitic emf voltage) given as:

$$X(t)=2/T\int_{t-T}^{t}R_{XY}(t)\cos\omega_{REF}t\ dt$$

$$X(t)=2/T\int_{t-T}^{t}R_{XY}(t)\sin\omega_{REF}t\ dt$$

where T is the integration period equal to multiple of lock-in time constant $\tau$ which can be adjusted by the signal processing software.

The Hall signal then needs to be inspected in the frequency domain to see if there is signal at $f_{REF}$. For this, Fourier transform and power spectral density (PSD) analyses are performed. PSD analysis enhances the periodic (i.e. the desired Hall signal) in the raw signal as PSD may be equal to a Fourier transform of an auto correlation of the signal. The software will then calculate and generate a report of the final results as well as the S/N ratio in the measurement.

$$X=B_{max}/nde,\ Y=B_{max}107\ A/I_S,\ n=B_{max}/Xde,\ \mu=1/ne\rho$$

where $\rho$ is the resistivity of the sample that can obtained from longitudinal van der Pauw measurement. The signal to noise ratio is given as: $S/N=<X(t)^2>/<R_{XY}^2(t)>$.

Thus, returning to FIG. 6, the method includes a determination of whether or not the Hall power spectral density (PSD) has a peak that exists at $f_{REF}$ (operation 606). Then, in an event the Hall power spectral density (PSD) does not have a peak that exists at $f_{REF}$, the method includes an increase of acquisition time or a fix of a faulty contact/device (operation 607) whereupon control returns to operation 602. Alternatively, in an event the Hall power spectral density (PSD) has a peak that exists at $f_{REF}$, the method includes performance of a lock-in detection to the Hall signal with an extraction of in-phase (X) and out-of-phase (Y) signal components and a calculation of a signal to noise ratio (S/N) (operation 608).

Once operation 608 is completed, a determination of whether the out-of-phase (Y) signal is much greater than the in-phase (X) signal is made (operation 609). Then, in an event the out-of-phase (Y) signal is determined to be much greater than the in-phase (X) signal, the motor frequency $f_{REF}$ is reduced or the sample current $I_S$ is increased (operation 610) and control returns to operation 603. Alternatively, in an event the out-of-phase (Y) signal is determined to not be much greater than the in-phase (X) signal, final results are calculated (operation 611). The final results relate to whether the DUT 2052 is an N or P-type carrier, the carrier mobility and the carrier density.

As shown in FIG. 7, the control software may also generate on a display unit a user interface 700 by a user can monitor at least the Hall measurement. Such user interface 700 may include at least a readout of the magnetic field 701 in and around the DUT 2052, a readout of the magnetic field with a Fourier transform applied thereto 702, the raw Hall signal $R_{XY}$ 703, the Hall power spectral density (PSD) 704 for checking of the validity of the raw Hall signal $R_{XY}$ 703, the lock-in output X, Y and S/N 705 and an adjustable lock-in time constant 706.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method of operating a rotating magnetic field Hall apparatus, the method comprising:
    dispsosing first and second magnets in a master-slave configuration;
    interposing a device-under-test (DUT) stage between the first and second magnets;
    disposing a DUT on the DUT stage in first or second orientations for Hall measurement or photoelectromagnetic (PEM) testing, respectively;
    maneuvering the first magnet in a vertical dimension and maneuvering the second magnet in the vertical dimension and in a horizontal dimension to center the DUT stage between the first and second magnets;

disposing a first sensor on a first spire to face upwardly in the vertical dimension to face a lower facing lateral and non-longitudinal side of the first magnet;

disposing a second sensor on a second spire to face sideways in the horizontal dimension to face a sideways facing lateral and non-longitudinal side of the first magnet;

facilitating positional initialization of the first and second magnets; and generating in-phase and out-of-phase reference signals for phase-sensitive or lock-in Hall signal detection.

2. The method according to claim 1, further comprising disposing the first and second magnets in parallel.

3. The method according to claim 1, further comprising increasing a magnetic field of one of the first and second magnets.

4. The method according to claim 3, further comprising:
interposing a first magnetic flux concentrator between the first magnet and the DUT stage along the vertical dimension; and
interposing a second magnetic flux concentrator between the second magnet and the DUT stage along the vertical dimension.

5. The method according to claim 1, further emitting light toward the DUT and applying current to the DUT.

6. A method of operating a computing system comprising a processor and a memory on which a program is stored, which, when executed causes the processor to manage a rotating magnet Hall apparatus, comprising:
first and second magnets disposed in a master-slave configuration; and
a device-under-test (DUT) stage interposable between the first and second magnets on which a DUT is disposable in first or second orientations for Hall measurement or photoelectromagnetic (PEM) testing, respectively, the method comprising:
maneuvering the first magnet in a vertical dimension and maneuvering the second magnet in the vertical dimension and in a horizontal dimension to center the DUT stage between the first and second magnets; and
operating orthogonal magnetic field sensor assembly, comprising:
first and second transversely oriented spires;
a first sensor disposed on the first spire to face upwardly in the vertical dimension to face a lower facing lateral and non-longitudinal side of the first magnet; and
a second sensor disposed on the second spire to face sideways in the horizontal dimension to face a sideways facing lateral and non-longitudinal side of the first magnet,
the first and second sensors being configured to facilitate positional initialization of the first and second magnets and to generate in-phase and out-of-phase reference signals for phase-sensitive or lock-in Hall signal detection.

7. The method according to claim 6, wherein the processor is configured to perform signal processing to extract a final Hall signal and comprises:
a signal conditioning system for data selection and background subtraction;
a power spectral density analysis system; and
a system for lock-in detection and signal-to-noise ratio calculation.

* * * * *